US011835618B2

(12) United States Patent
Horng et al.

(10) Patent No.: US 11,835,618 B2
(45) Date of Patent: Dec. 5, 2023

(54) MULTIPLE-TARGET VITAL SIGN DETECTOR AND DETECTION METHOD USING THE SAME

(71) Applicant: NATIONAL SUN YAT-SEN UNIVERSITY, Kaohsiung (TW)

(72) Inventors: Tzyy-Sheng Horng, Kaohsiung (TW); Fu-Kang Wang, Kaohsiung (TW); Wei-Chih Su, Kaohsiung (TW); Mu-Cyun Tang, Kaohsiung (TW); Rezki El Arif, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 729 days.

(21) Appl. No.: 17/064,707

(22) Filed: Oct. 7, 2020

(65) Prior Publication Data
US 2021/0109208 A1    Apr. 15, 2021

(30) Foreign Application Priority Data

Oct. 9, 2019  (TW) .................................. 108136765

(51) Int. Cl.
*G01S 13/89* (2006.01)
*A61B 5/05* (2021.01)
(Continued)

(52) U.S. Cl.
CPC .............. *G01S 13/89* (2013.01); *A61B 5/05* (2013.01); *G01S 7/35* (2013.01); *A61B 5/0205* (2013.01);
(Continued)

(58) Field of Classification Search
CPC .......... G01S 13/89; G01S 7/35; G01S 13/584; G01S 13/34; A61B 5/05; A61B 5/0205; A61B 5/02444; A61B 5/0816
See application file for complete search history.

(56) References Cited

U.S. PATENT DOCUMENTS

| 5,495,252 A | 2/1996 | Adler |
| 9,375,153 B2 | 6/2016 | Horng et al. |

(Continued)

FOREIGN PATENT DOCUMENTS

| CN | 108072864 A | 5/2018 |
| TW | 201417052 A | 5/2014 |

(Continued)

OTHER PUBLICATIONS

Taiwanese Office Action dated Apr. 19, 2021 for Taiwanese Patent Application No. 108136765, 3 pages.

(Continued)

*Primary Examiner* — Bernarr E Gregory
*Assistant Examiner* — Kenneth W Good
(74) *Attorney, Agent, or Firm* — Demian K. Jackson; Jackson IPG PLLC

(57) ABSTRACT

A multiple-target vital sign detector includes a self-injection-locked oscillator (SILO), a chirp up/down converter, a frequency demodulator and a multiple-target vital sign processor. The chirp up/down converter performs conversion from an oscillation signal generated by the SILO to a frequency-modulated continuous wave (FMCW) signal to detect an area and from a received FMCW signal reflected from the area to an injection signal, while the SILO is injected with the injection signal to enter a self-injection-locked state. The locations and vital signs of multiple subjects are extracted from the oscillation signal using the frequency demodulator and the multiple-target vital sign processor. The objective of using the SILO is to improve the sensitivity of the FMCW detection process so as to more effectively distinguish the vital signs of multiple subjects at different locations.

16 Claims, 9 Drawing Sheets

(51) Int. Cl.
 G01S 7/35 (2006.01)
 A61B 5/08 (2006.01)
 A61B 5/0205 (2006.01)
 A61B 5/024 (2006.01)

(52) U.S. Cl.
 CPC ......... *A61B 5/02444* (2013.01); *A61B 5/0816* (2013.01)

(56) References Cited

U.S. PATENT DOCUMENTS

| | | | | |
|---|---|---|---|---|
| 11,337,614 B2* | 5/2022 | Wu | ............... | A61B 5/7235 |
| 2009/0189740 A1* | 7/2009 | Wiesner | ............... | G08C 17/02 |
| | | | | 340/10.3 |
| 2010/0241009 A1* | 9/2010 | Petkie | ............... | G01S 7/35 |
| | | | | 342/147 |
| 2011/0279275 A1* | 11/2011 | Horng | ............... | G01S 13/88 |
| | | | | 702/66 |
| 2012/0209087 A1* | 8/2012 | Horng | ............... | G01S 13/87 |
| | | | | 600/301 |
| 2013/0321198 A1* | 12/2013 | Park | ............... | G01S 13/878 |
| | | | | 342/175 |
| 2017/0172425 A1* | 6/2017 | Liu | ............... | A61B 5/05 |
| 2019/0146091 A1* | 5/2019 | Matsko | ............... | H01S 5/141 |
| | | | | 356/5.01 |
| 2021/0026002 A1* | 1/2021 | Saric | ............... | G01S 13/40 |

FOREIGN PATENT DOCUMENTS

| | | |
|---|---|---|
| TW | 201901181 A | 1/2019 |
| TW | I669913 B | 8/2019 |
| WO | 2015/184406 A1 | 12/2015 |

OTHER PUBLICATIONS

Wei-Chih Su et al., Single Conversion Stepped-Frequency Continuous-Wave Radar Using Self-Injection-Locking Technology, 2019 IEEE/MTT-S International Microwave Symposium, Jun. 2-7, 2019.

Wei-Chih Su et al., Stepped-Frequency Continuous-Wave Radar with Self-Injection-Locking Technology for Monitoring Multiple Human Vital Signs, IMS2019 TMTT Manuscript, Aug. 21, 2019.

* cited by examiner

MULTIPLE-TARGET VITAL SIGN DETECTOR AND DETECTION METHOD USING THE SAME

FIELD OF THE INVENTION

This invention generally relates to a vital sign detector, and more particularly to a multiple-target vital sign detector.

BACKGROUND OF THE INVENTION

In general, non-contact vital sign detector transmits a wireless signal to a subject and receives an echo signal from the subject so as to detect vital signs of the subject based on the Doppler effect caused by the physiological movements of the subject. However, the conventional vital sign detector can only detect vital signs of a single subject, multiple-target vital sign detection is not practical due to the interference among the echo signals from the multiple subjects.

The frequency-modulated continuous wave (FMCW) radar transmits a signal increasing in frequency over time to a subject and receives an echo signal from the subject. It is commonly used to measure the distance of the subject from the radar by the frequency difference between the transmitted and echo signals at the same instant. Nevertheless, the sensitivity of the FMCW radar is usually low and insufficient to detect the subject's tiny movements due to vital signs.

SUMMARY

The present invention discloses a multiple-target vital sign detector that uses a self-injection-locked oscillator (SILO) in an FMCW radar to greatly improve the sensitivity in detecting vital signs of multiple subjects at different distances from the detector simultaneously.

One aspect of the present invention provides a multiple-target vital sign detector including a SILO, a chirp up/down converter, a frequency demodulator and a multiple-target vital sign processor. The SILO is provided to generate an oscillation signal. The chirp up/down converter includes an upconverting mixer, a transceiver antenna, a downconverting mixer and a chirp signal generator. The upconverting mixer is electrically connected to the SILO and the chirp signal generator to convert the oscillation signal into an FMCW signal. The transceiver antenna is electrically connected to the upconverting mixer to transmit the FMCW signal as a transmitted signal to an area. Then the transceiver antenna receives a reflected signal from the area as a received FMCW signal. The downconverting mixer is electrically connected to the transceiver antenna to convert the received FMCW signal into an injection signal. The SILO is electrically connected to the downconverting mixer to receive the injection signal and thereby enters a self-injection-locked state. The frequency demodulator is electrically connected to the SILO to frequency demodulate the oscillation signal as a frequency-demodulated signal. The multiple-target vital sign processor is electrically connected to the frequency demodulator to sample and process the frequency-demodulated signal to construct a range-vital-Doppler map.

Another aspect of the present invention provides a detection method using a multiple-target vital sign detector. The detection method includes the steps of: generating an oscillation signal using a SILO; performing conversion from the oscillation signal to an FMCW signal to detect an area and from a received FMCW signal reflected from the area to an injection signal using a chirp up/down converter; injecting the injection signal into the SILO to achieve a self-injection-locked state of the SILO; frequency-demodulating the oscillation signal to produce a frequency-demodulated signal using a frequency demodulator; and sampling and processing the frequency-demodulated signal to construct a range-vital-Doppler map using a multiple-target vital sign processor.

The multiple-target vital sign detector of the present invention uses the SILO to provide high sensitivity of vital sign detection. Moreover, the multiple-target vital sign detector can distinguish the vital signs of multiple subjects using their range information based on FMCW technology.

DETAILED DESCRIPTION OF THE INVENTION

Figure 1:
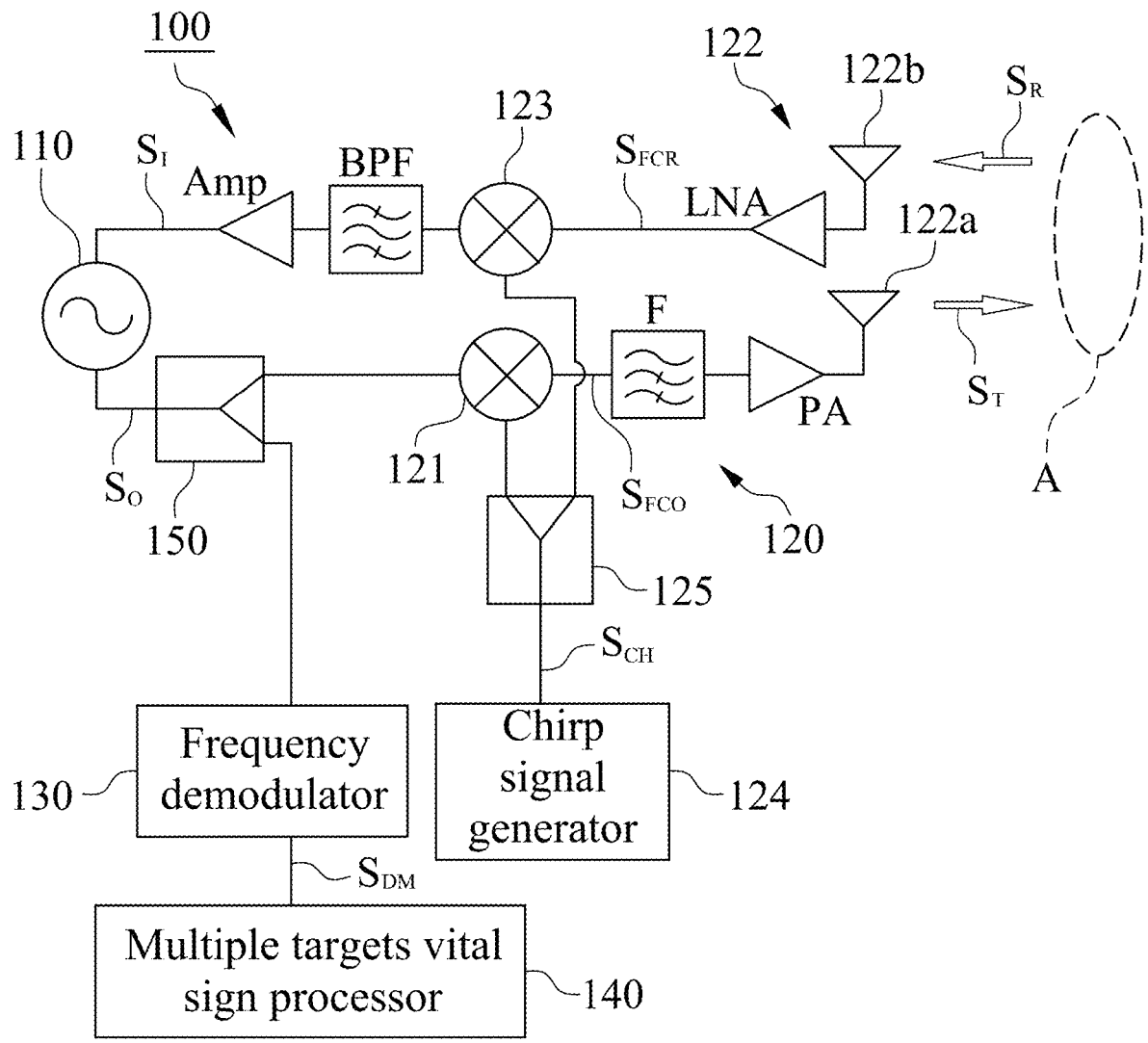
FIG. 1 is a circuit diagram illustrating a multiple-target vital sign detector in accordance with a first embodiment of the present invention.

A multiple-target vital sign detector 100 in accordance with a first embodiment of the present invention is shown in FIG. 1. The multiple-target vital sign detector 100 includes a SILO 110, a chirp up/down converter 120, a frequency demodulator 130, a multiple-target vital sign processor 140 and a first power splitter 150.

The SILO 110 in the first embodiment is a voltage-controlled oscillator that is provided to generate an oscillation signal $S_O$ according to a control voltage (not shown). The first power splitter 150 is electrically connected to the SILO 110 to split the oscillation signal $S_O$ into two parts.

With reference to FIG. 1, the chirp up/down converter 120 includes an upconverting mixer 121, a transceiver antenna 122, a downconverting mixer 123, a chirp signal generator 124 and a second power splitter 125. The second power splitter 125 is electrically connected to the chirp signal generator 124 to split a chirp signal $S_{CH}$ generated by the chirp signal generator 124 into two parts. The upconverting mixer 121 is electrically connected to the first power splitter 150 and the second power splitter 125 such that it can receive one part of the oscillation signal $S_O$ from the first power splitter 150 and one part of the chirp signal $S_{CH}$ from the second power splitter 125. The upconverting mixer 121 is provided to mix the oscillation signal $S_O$ with the chirp signal $S_{CH}$ to obtain an FMCW signal $S_{FCO}$. The FMCW signal $S_{FCO}$ can be changed to a stepped-frequency continuous wave (SFCW) signal when a stepped chirp signal is generated by the chirp signal generator 124.

With reference to FIG. 1, the transceiver antenna 122 is coupled to the upconverting mixer 121 via a filter F and a power amplifier PA to transmit the FMCW signal $S_{FCO}$ from the upconverting mixer 121 toward an area A as a transmitted signal $S_T$. The filter F is provided to filter out spurious components in the FMCW signal $S_{FCO}$ and the power amplifier PA is provided to amplify the FMCW signal $S_{FCO}$. The transceiver antenna 122 receives a reflected signal $S_R$ from the area A as a received FMCW signal $S_{FCR}$. The downconverting mixer 123 is electrically connected to the transceiver antenna 122 via a low-noise amplifier LNA to receive the received FMCW signal $S_{FCR}$ and also receives the other part of the chirp signal $S_{CH}$ from the second power splitter 125. Thus, the received FMCW signal $S_{FCR}$ is amplified by the low-noise amplifier LNA and then converted into an injection signal $S_I$ by mixing with the chirp signal $S_{CH}$ in the downconverting mixer 123. In this embodiment, the transceiver antenna 122 includes a transmit antenna 122a and a receive antenna 122b that are electrically connected to the upconverting mixer 121 and the downconverting mixer 123, respectively. The FMCW signal $S_{FCO}$ from the upconverting mixer 121 is transmitted toward the area A by the transmit antenna 122a as the transmitted signal $S_T$. The reflected signal $S_R$ is received from the area A by the receive antenna 122b as the received FMCW signal $S_{FCR}$. The received FMCW signal $S_{FCR}$ is delivered from the receive antenna 122b to the downconverting mixer 123.

With reference to FIG. 1, the SILO 110 is electrically connected to the downconverting mixer 123 via a bandpass filter BPF and an amplifier Amp to receive the injection signal $S_I$ to enter a self-injection-locked state. The amplifier Amp is provided to amplify the injection signal $S_I$ while the bandpass filter BPF is used to suppress the spurious components in the injection signal $S_I$.

The Doppler effect occurs in the transmitted signal $S_T$ when a subject in the area A has a displacement with respect to the transceiver antenna 122. Accordingly, the reflected signal $S_R$ contains the Doppler phase shift caused by the displacement of the subject. Since the transmitted signal $S_T$ is a linear chirp whose frequency varies linearly with time, the detection of multiple subjects at different distances in the area A leads to different frequency differences between the reflected signal $S_R$ and the transmitted signal $S_T$. Accordingly, the received FMCW signal $S_{FCR}$ and the injection signal $S_I$ both contain the range and displacement information of the multiple subjects in the area A. Moreover, the injection signal $S_I$ is injected into the SILO 110 to frequency-modulate the oscillation signal $S_O$ of the SILO 110 with the range and displacement information of the multiple subjects in the area A.

With reference to FIG. 1, the frequency demodulator 130 that is electrically connected to the SILO 110 via the first power splitter 150 receives and frequency-demodulates the other part of the oscillation signal $S_O$ to produce a frequency-demodulated signal $S_{DM}$. The frequency demodulator 130 may be a delay-line frequency demodulator or a phase-locked loop frequency demodulator.

Figure 2:
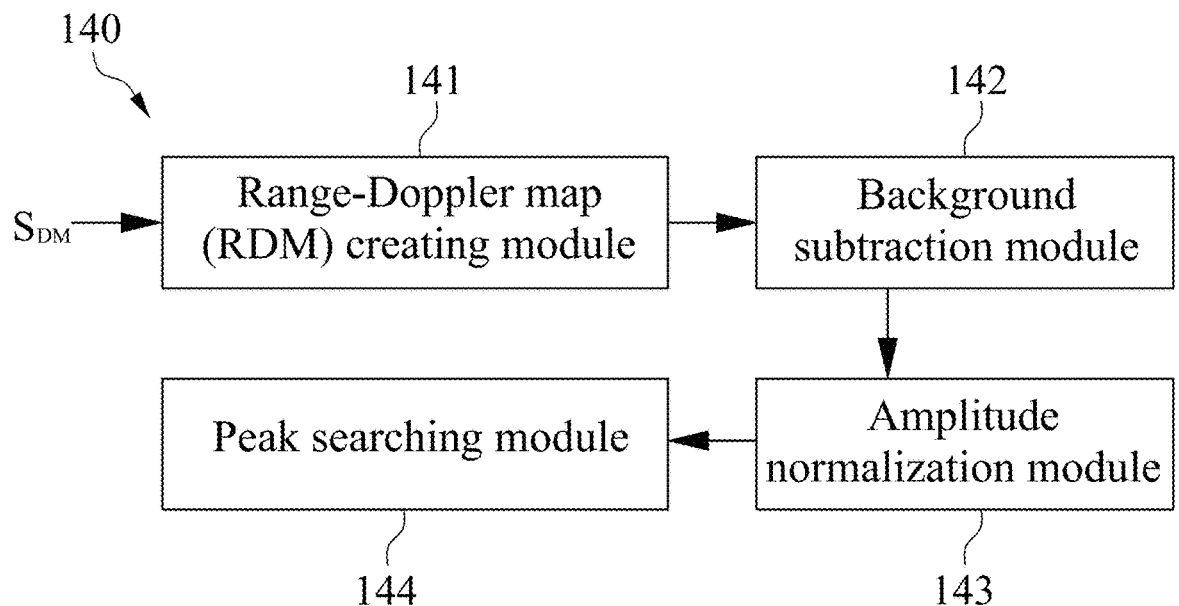
FIG. 2 is a block diagram illustrating a multiple-target vital sign processor in accordance with the first embodiment of the present invention.

With reference to FIGS. 1 and 2, the multiple-target vital sign processor 140 includes a range-Doppler map (RDM) creating module 141, a background subtraction module 142, an amplitude normalization module 143 and a peak searching module 144. In this embodiment, the multiple-target vital sign processor 140 is a data acquisition and computing system. The multiple-target vital sign processor 140 may be different in other embodiments.

Figure 3:
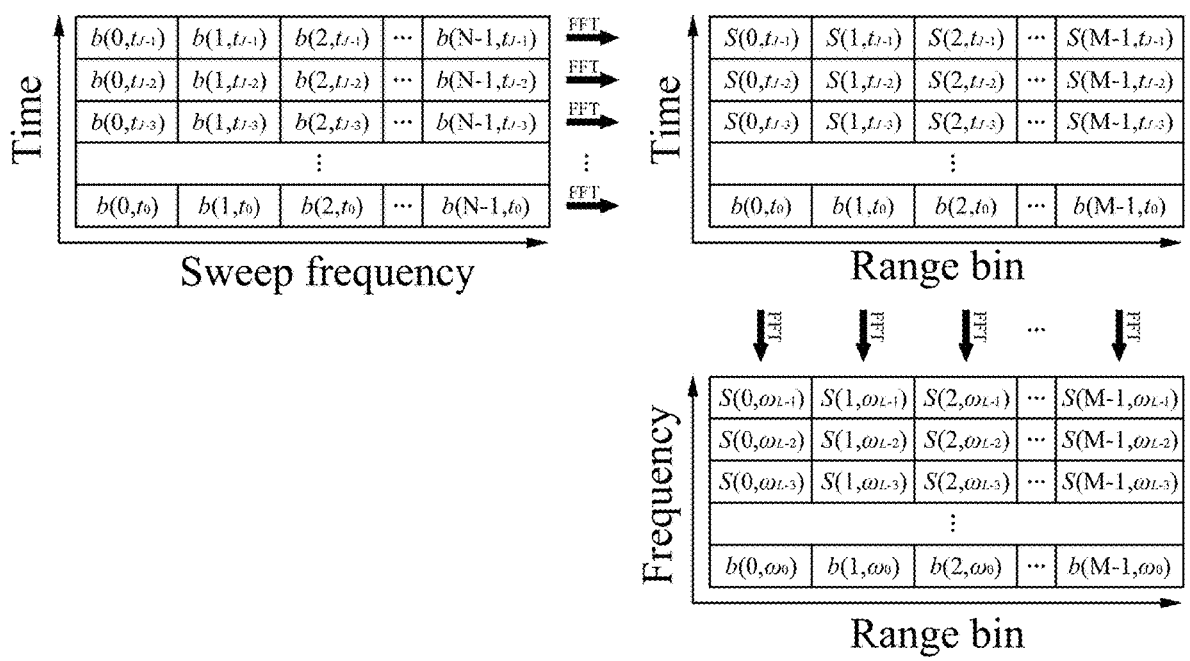
FIG. 3 is a diagram illustrating a signal processing procedure by using an RDM creating module in accordance with the first embodiment of the present invention.

With reference to FIG. 2, the RDM creating module 141 samples and processes the frequency-demodulated signal $S_{DM}$ from the frequency demodulator 130 to create an RDM. As shown in FIG. 3, the processing procedure of the RDM begins with the construction of a J×N raw data (time versus frequency step) matrix as the top-left of FIG. 3, where J is the total number of frequency sweeps at different times and N is the total number of frequency steps. Then a first fast Fourier transform is applied to each row of the raw data matrix to obtain a J×M range profile (time versus range bin) matrix as the top-right of FIG. 3, where M is the maximum range bin number. Finally, a second fast Fourier transform is applied to each column of the range profile matrix to get an L×M range-Doppler (frequency versus range bin) matrix as the bottom-right of FIG. 3, where L is the maximum frequency index. The RDM is produced by using the range-Doppler matrix to present Doppler spectra of objects at different distances.

However, the vital signs of the subjects are hard to identify by using the RDM because of interferences from static objects. Therefore, the RDM is further processed using the background subtraction module 142, the amplitude normalization module 143 and the peak searching module 144 in this embodiment. The background subtraction module 142 receives the RDM at different times from the RDM creating module 141 and eliminates a background of the RDM to create a background-subtracted RDM. The Doppler spectra resulting from the vital sign signals of the subjects vary with time and are different from those of static objects which are time invariant. As a result, the background-subtracted RDM can be used to eliminate the interferences from static objects to more easily identify the vital signs of the subjects.

The amplitude normalization module 143 receives and normalizes the background-subtracted RDM in amplitude to create a normalized background-subtracted RDM. Through amplitude normalization, the maximum spectral amplitude of each subject's vital sign signal is identical to benefit the display of respiration and heartbeat frequencies of each subject, no matter how far each subject may stay. The peak searching module 144 searches for peaks above a certain threshold in the normalized background-subtracted RDM to construct a range-vital-Doppler map that displays simultaneously the range and vital sign frequency information of the subjects.

In the multiple-target vital sign detector 100 of the present invention, the objective of using the SILO 110 is to improve the sensitivity of the FMCW detection process so as to more effectively distinguish the vital signs of multiple subjects at different distances from the multiple-target vital sign detector 100.

Figure 4:
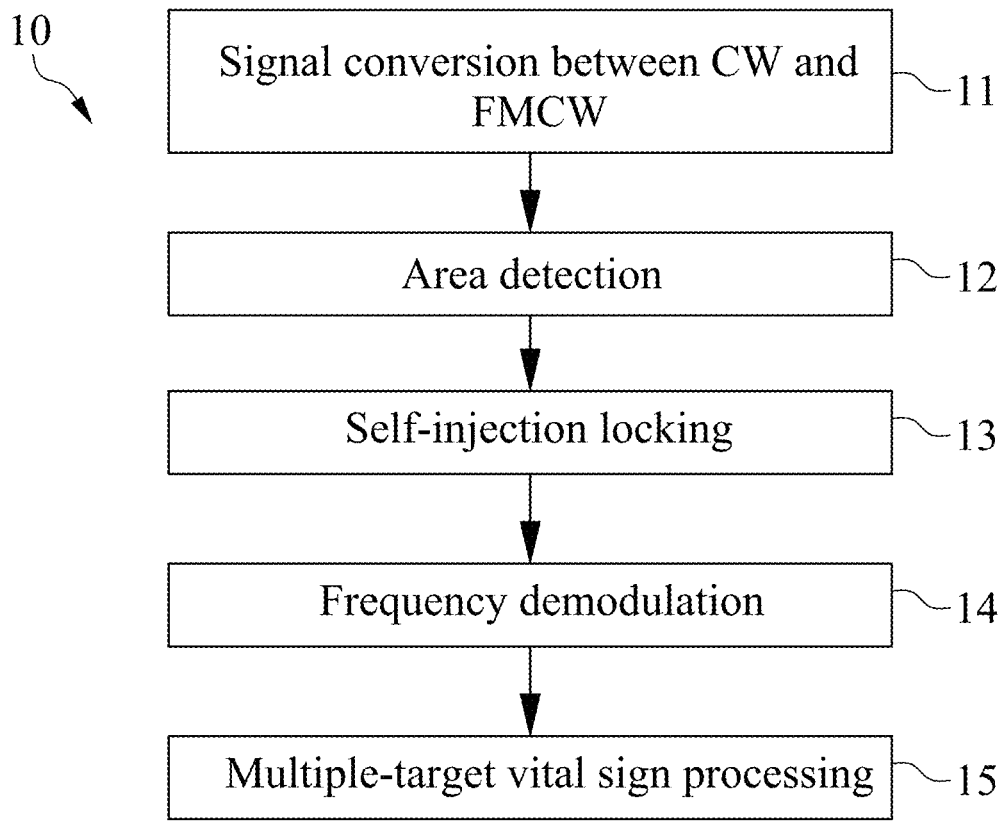
FIG. 4 is a flowchart illustrating a detection method using the multiple-target vital sign detector in accordance with the first embodiment of the present invention.

With reference to FIG. 4, a detection method 10 using the multiple-target vital sign detector 100 of the present invention includes a step 11 for signal conversion between continuous wave (CW) and FMCW, a step 12 for area detection, a step 13 for self-injection-locking and a step 14 for multiple-target vital sign processing.

With reference to FIGS. 1 and 4, by using the chirp up/down converter 120, the FMCW signal $S_{FCO}$ results from the conversion of the oscillation signal $S_O$ which is a CW signal in the step 11 and is transmitted to the area A as the transmitted signal $S_T$ for vital sign detection in the step 12. In the chirp up/down converter 120, as shown in FIG. 1, the upconverting mixer 121 receives the oscillation signal $S_O$ from the SILO 110 via the first power splitter 150 and the chirp signal $S_{CH}$ from the chirp signal generator 124 via the second power splitter 125 to convert the oscillation signal $S_O$ into the FMCW signal $S_{FCO}$. The transmit antenna 122a transmits the FMCW signal $S_{FCO}$ from the upconverting mixer 121 to the area A as the transmitted signal $S_T$, and the receive antenna 122b receives the reflected signal $S_R$ from the area A as the received FMCW signal $S_{FCR}$. The downconverting mixer 123 receives the received FMCW signal $S_{FCR}$ from the receive antenna 122b and the chirp signal $S_{CH}$ from the chirp signal generator 124 via the second power splitter 125 to convert the received FMCW signal $S_{FCR}$ into the injection signal $S_I$.

With reference to FIGS. 1 and 4, the SILO 110 is injected with the injection signal $S_I$ to enter the self-injection-locked state in the step 13. If there is at least one subject in the area A, a frequency modulation with respect to the range and displacement information of the subject is applied to the oscillation signal $S_O$ of the SILO 110. In the step 14, the frequency demodulator 130 receives the oscillation signal $S_O$ from the SILO 110 via the first power splitter 150 and frequency-demodulates the oscillation signal $S_O$ to produce the frequency-demodulated signal $S_{DM}$. Finally, in the step 15, the multiple-target vital sign processor 140 samples and processes the frequency-demodulated signal $S_{DM}$ from the frequency demodulator 130 to construct the range-vital-Doppler map.

Figure 5:
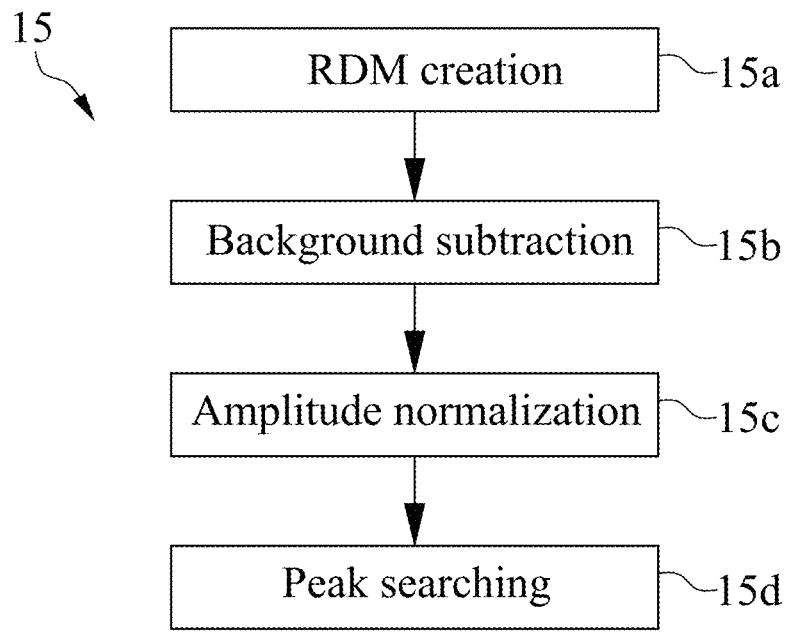
FIG. 5 is a flowchart illustrating a processing procedure of the multiple-target vital sign processor in accordance with the first embodiment of the present invention.

With reference to FIGS. 2 and 5, in this embodiment, the step 15 performed by the multiple-target vital sign processor 140 includes a sub-step 15a for RDM creation, a sub-step 15b for background subtraction, a sub-step 15c for amplitude normalization and a sub-step 15d for peak searching. The RDM creating module 141 samples and processes the frequency-demodulated signal $S_{DM}$ from the frequency demodulator 130 to create the RDM in the sub-step 15a. The background subtraction module 142 eliminates the background of the RDM to create the background-subtracted RDM in the sub-step 15b. The amplitude normalization module 143 normalizes the background-subtracted RDM in amplitude to create the normalized background-subtracted RDM in the sub-step 15c. And last, in the sub-step 15d, the peak searching module 144 searches for the peaks above a certain threshold in the normalized background-subtracted RDM to construct the range-vital-Doppler map. The details of the detection method 10 are like the above description regarding the multiple-target vital sign detector 100 and will not be repeated here.

Figure 6:
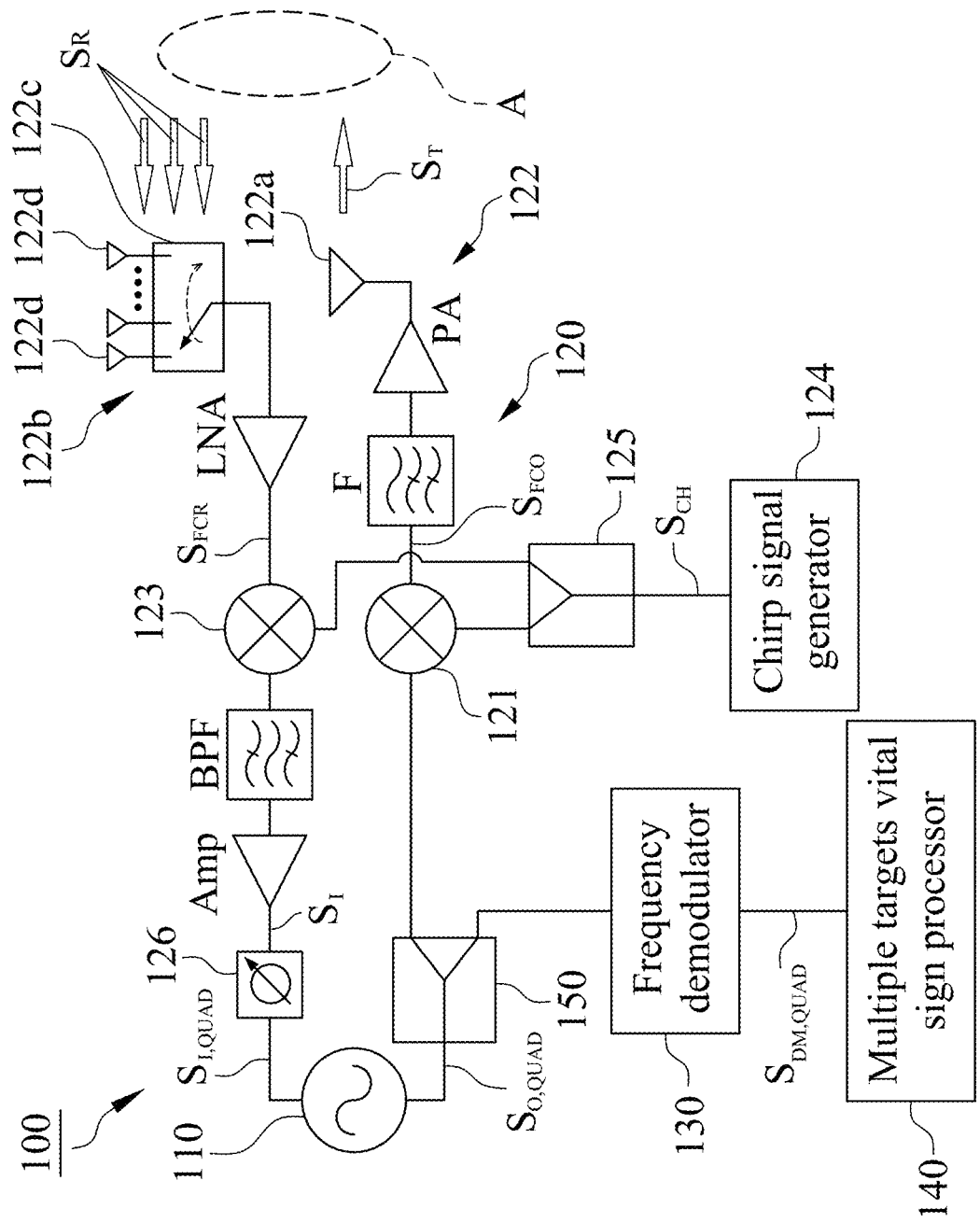
FIG. 6 is a circuit diagram illustrating a multiple-target vital sign detector in accordance with a second embodiment of the present invention.

FIG. 6 shows a multiple-target vital sign detector 100 of a second embodiment of the present invention. In the second embodiment, the chirp up/down converter 120 further includes a phase shifter 126. Additionally, the receive antenna 122b is a switched antenna array composed of a switch 122c and a plurality of receive array antenna elements 122d. The receive array antenna elements 122d are arranged to receive the reflected signal $S_R$ from the area A as the received FMCW signal $S_{FCR}$. Consequently, further information about the positions of the subjects in the area A can be obtained.

The switch 122c is electrically connected to the downconverting mixer 123 and the receive array antenna elements 122d, and thus the received FMCW signal $S_{FCR}$ from the receive array antenna elements 122d is delivered via the switch 122c to the downconverting mixer 123. Subsequently, the received FMCW signal $S_{FCR}$ is converted into the injection signal $S_I$ by mixing with the chirp signal $S_{CH}$ coming from the chirp signal generator 124 via the second power splitter 125.

The phase shifter 126 is electrically connected to the downconverting mixer 123 and the SILO 110 and provided to shift the phase of the injection signal $S_I$ by 0 or 90 degrees to produce a quadrature phase-shifted injection signal $S_{I,QUAD}$. The quadrature phase-shifted injection signal $S_{I,QUAD}$ is then injected into the SILO 110 to make the SILO 110 enter the self-injection-locked state. Accordingly, under the self-injection-locked state, the SILO 110 generates a quadrature phase-shifted oscillation signal $S_{O,QUAD}$. In the transmission path, the quadrature phase-shifted oscillation signal $S_{O,QUAD}$ is delivered via the first power splitter 150 to the upconverting mixer for mixing with the chirp signal $S_{CH}$ coming from the chirp signal generator 124 via the second power splitter 125 to obtain the FMCW signal $S_{FCO}$.

The frequency demodulator 130 frequency demodulates the quadrature phase-shifted oscillation signal $S_{O,QUAD}$ from the SILO 110 via the first power splitter 150 to produce a quadrature frequency-demodulated signal $S_{DM,QUAD}$. The quadrature frequency-demodulated signal $S_{DM,QUAD}$ can be used by the multiple-target vital sign processor 140 to determine the phase difference between the receive array antenna elements 122d from which the azimuth angles of the subjects in the area A can be extracted using a digital beamforming technique.

Figure 7:
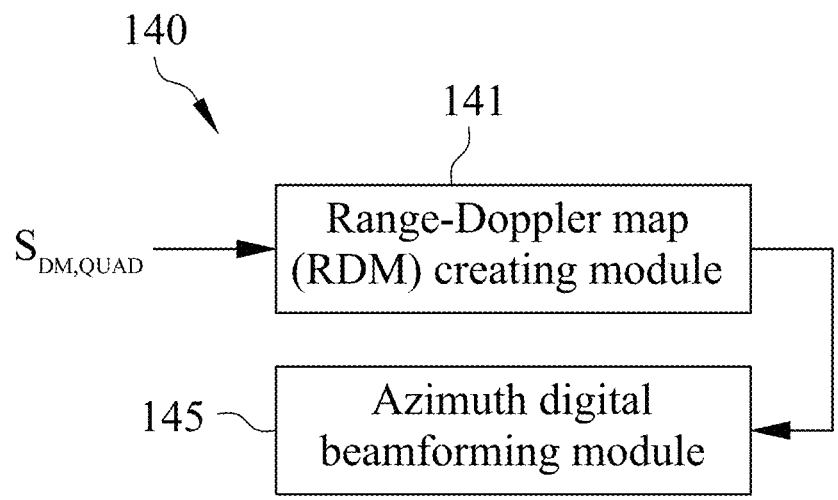
FIG. 7 is a block diagram illustrating a multiple-target vital sign processor in accordance with the second embodiment of the present invention.

With reference to FIG. 7, the multiple-target vital sign processor 140 of the second embodiment differs from that of the first embodiment by including the RDM creating module 141 and an azimuth digital beamforming module 145. The RDM creating module 141 samples and processes the quadrature frequency-demodulated signal $S_{DM,QUAD}$ from the frequency demodulator 130 to create the RDMs corresponding to the receive array antenna elements 122d. The azimuth digital beamforming module 145 is coupled to the RDM creating module 141 and extracts a range-azimuth map from the RDMs corresponding to the receive array antenna elements 122d using the digital beamforming technique.

The objective of the second embodiment is not only to distinguish the vital signs of multiple subjects at different distances by using the SILO 110 and the chirp up/down converter 120 in the multiple-target vital sign detector 100, but also to separate the vital signs of multiple subjects at different azimuth angles by additionally using the switch 122c, the receive array antenna elements 122d and the phase shifter 126 in the chirp up/down converter 120 of the multiple-target vital sign detector 100.

Figure 8:
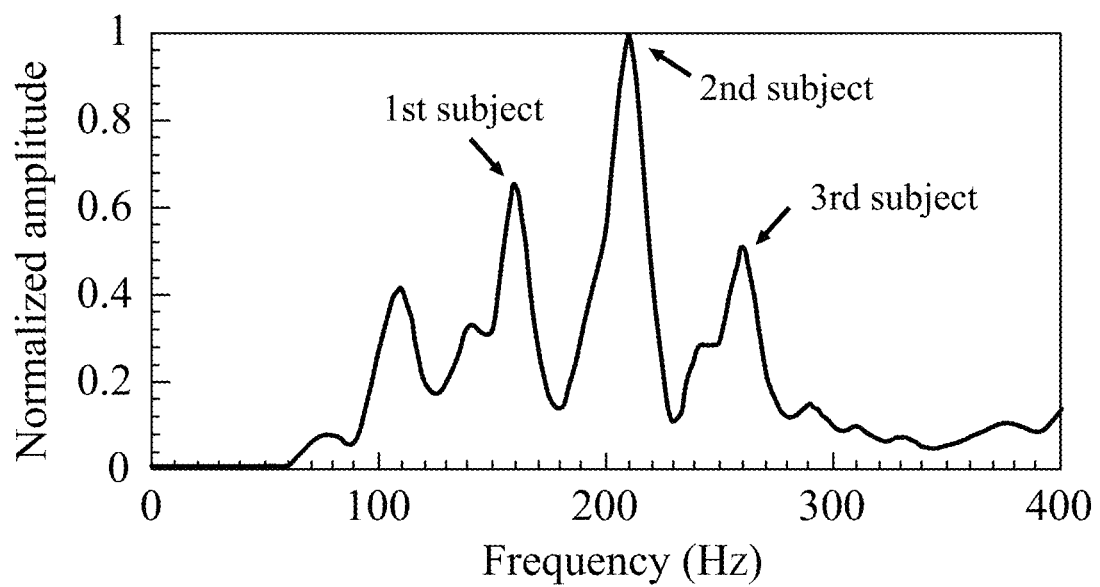
FIG. 8 shows the range spectrum obtained by the multiple-target vital sign detector in accordance with the first embodiment of the present invention.
Figure 9:
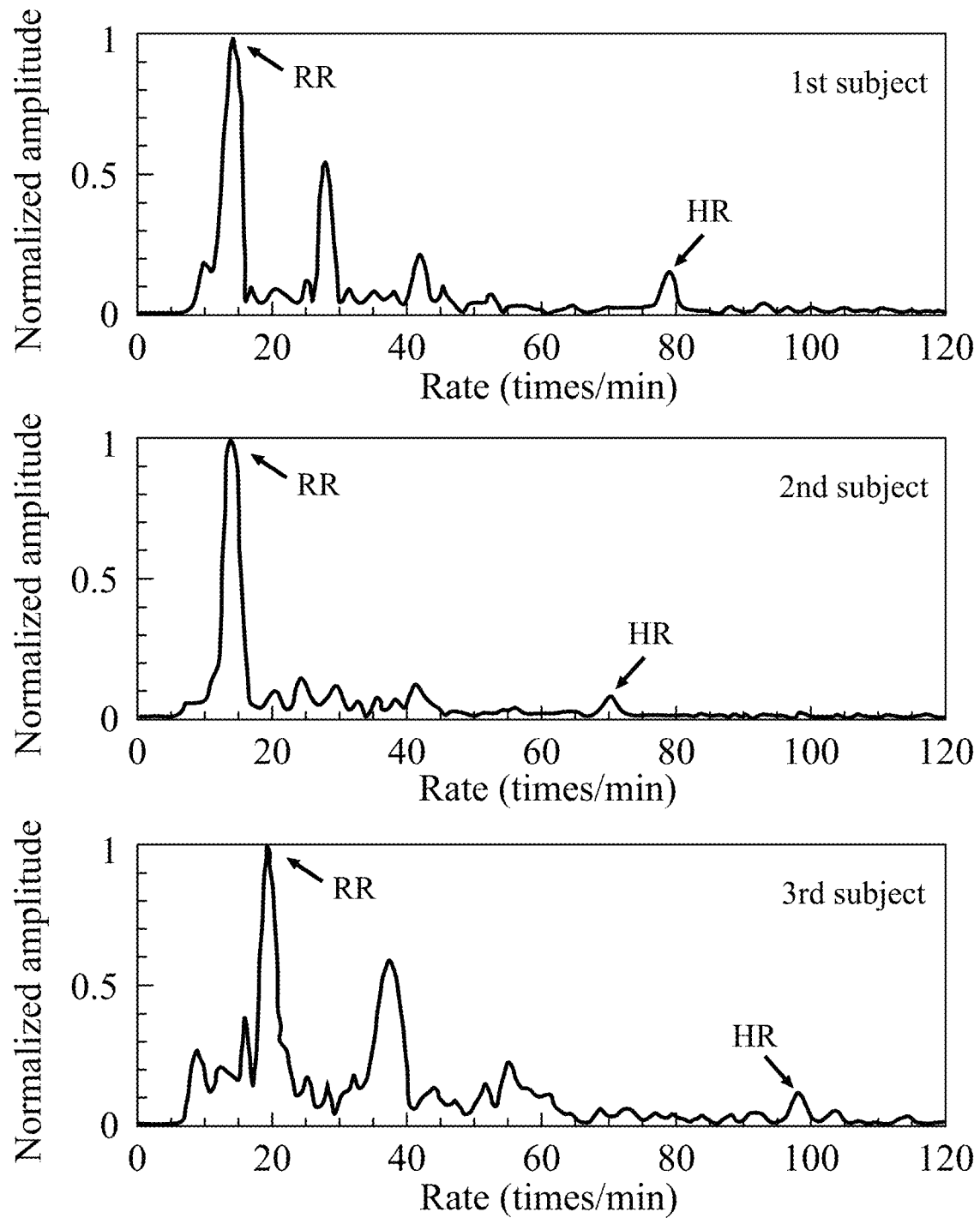
FIG. 9 shows the Doppler spectra obtained by the multiple-target vital sign detector in accordance with the first embodiment of the present invention.
Figure 10:
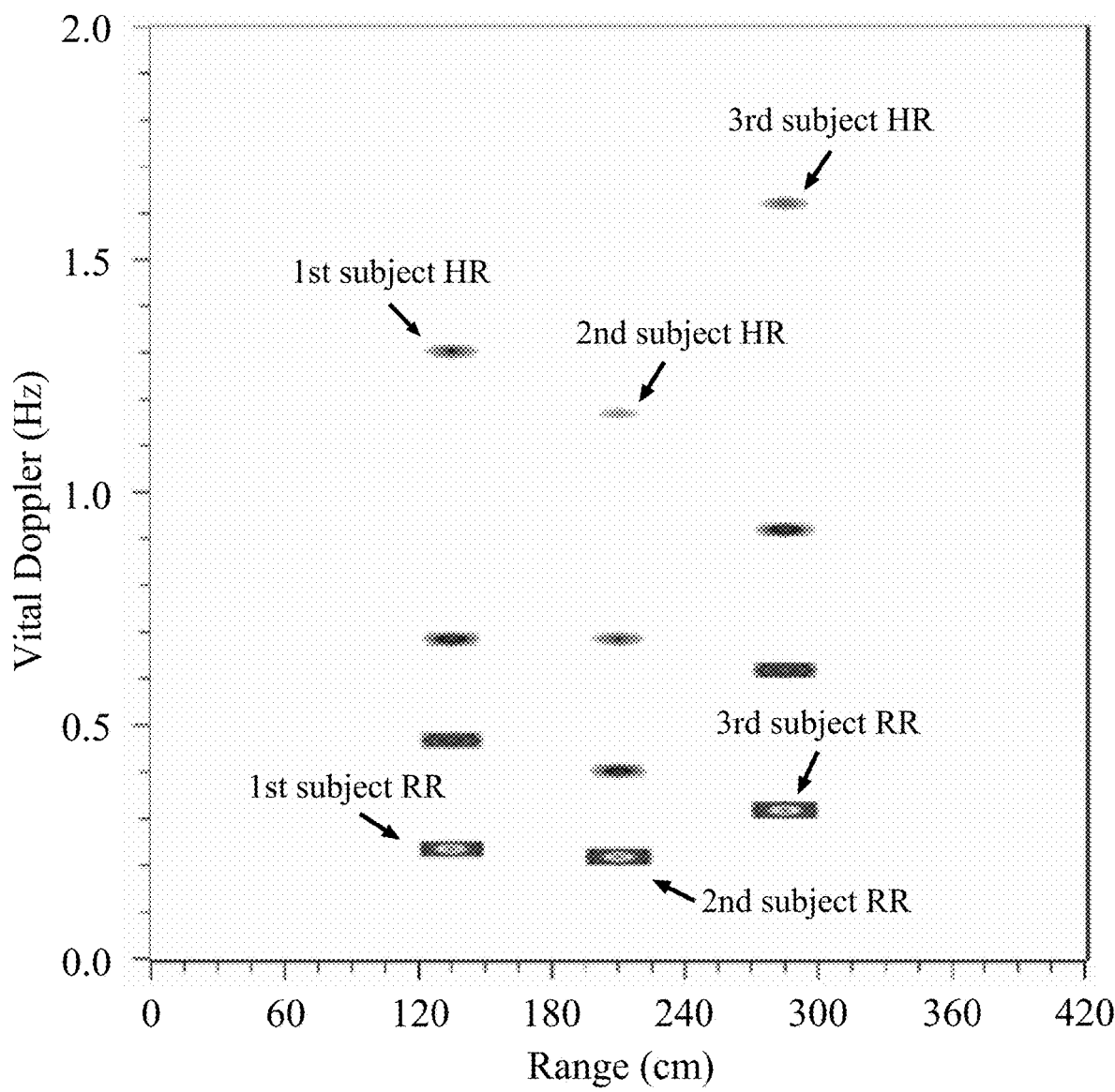
FIG. 10 is a range-vital-Doppler map constructed by the multiple-target vital sign detector in accordance with the first embodiment of the present invention.

FIGS. 8 to 10 are experimental results obtained by the multiple-target vital sign detector 100 of the first embodiment. There are three human subjects who are located at different distances from the multiple-target vital sign detector 100 and within a beamwidth of the transceiver antenna 122 in the chirp up/down converter 120 of the multiple-target vital sign detector 100. The subjects 1-3 are seated 135, 210 and 285 cm from the multiple-target vital sign detector 100, respectively. FIG. 8 shows the range spectrum acquired by applying the first fast Fourier transform to the frequency-demodulated signal $S_{DM}$. In the range spectrum of FIG. 8, the frequencies of the components with the highest three peaks are at 160, 210 and 260 Hz, corresponding to the distances of the subjects 1-3, respectively, from the multiple-target vital sign detector 100. FIG. 9 displays the Doppler spectra obtained by applying the second fast Fourier transform to the components of the range spectrum at 160, 210 and 260 Hz whose phases are time-varying. The frequency axes are replaced by rate axes in the Doppler spectra of FIG. 9, wherein a respiration rate (RR) and a heart rate (HR) of each of the subjects 1-3 are identified as the rate of the component having the highest peak in the range between 10 and 30 times/min and between 60 and 120 times/min, respectively, in corresponding each of the Doppler spectra.

FIG. 10 is a range-vital-Doppler map produced by the multiple-target vital sign processor 140. The range-vital-Doppler map simultaneously displays the distances and vital Doppler frequencies of the subjects 1-3. The vital Doppler frequencies from low to high at the distance of each of the subjects 1-3 are due to respiration, respiration harmonics and heartbeat.

Figure 11:
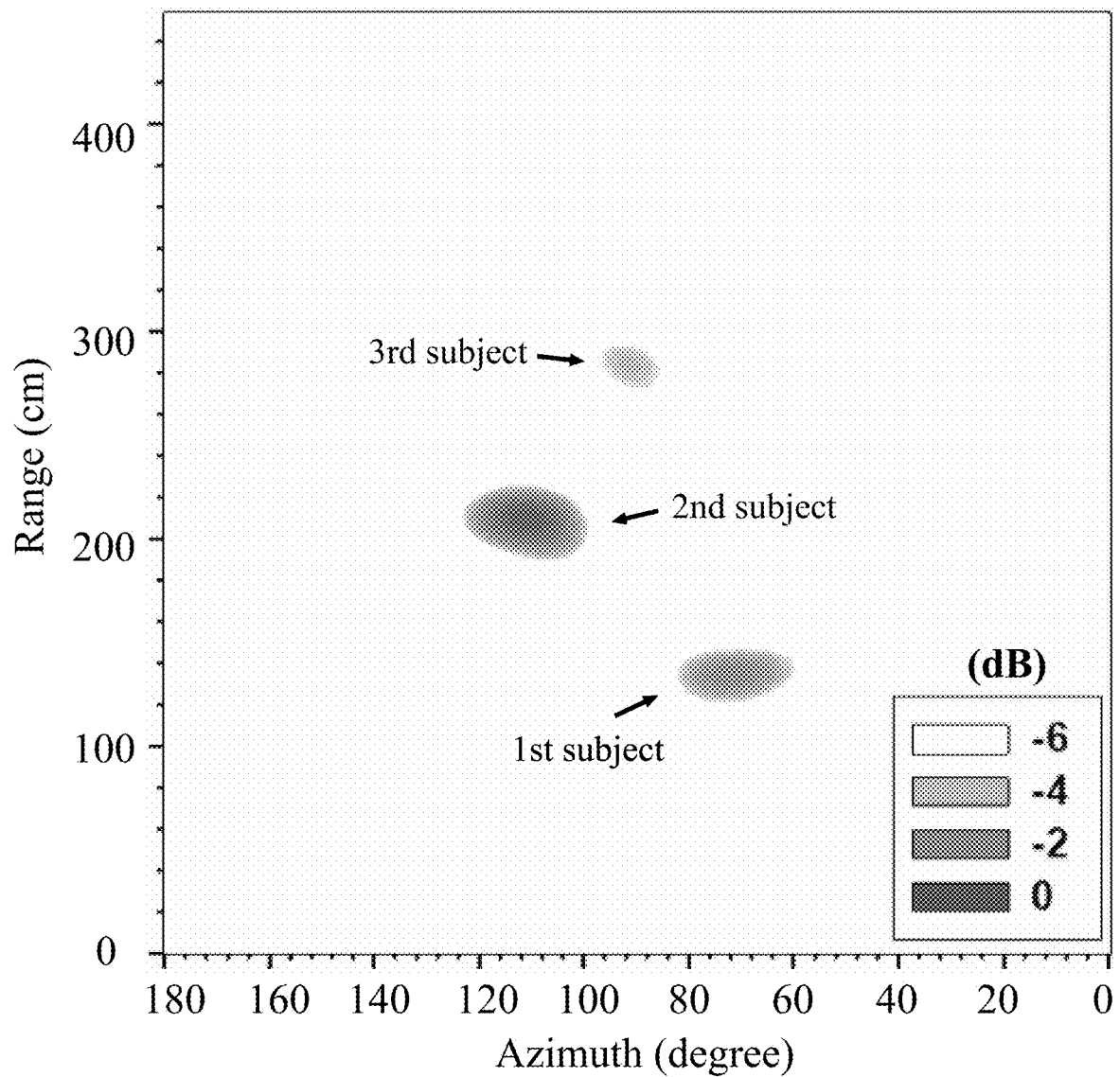
FIG. 11 is a range-azimuth map constructed by the multiple-target vital sign detector in accordance with the second embodiment of the present invention.
Figure 12:
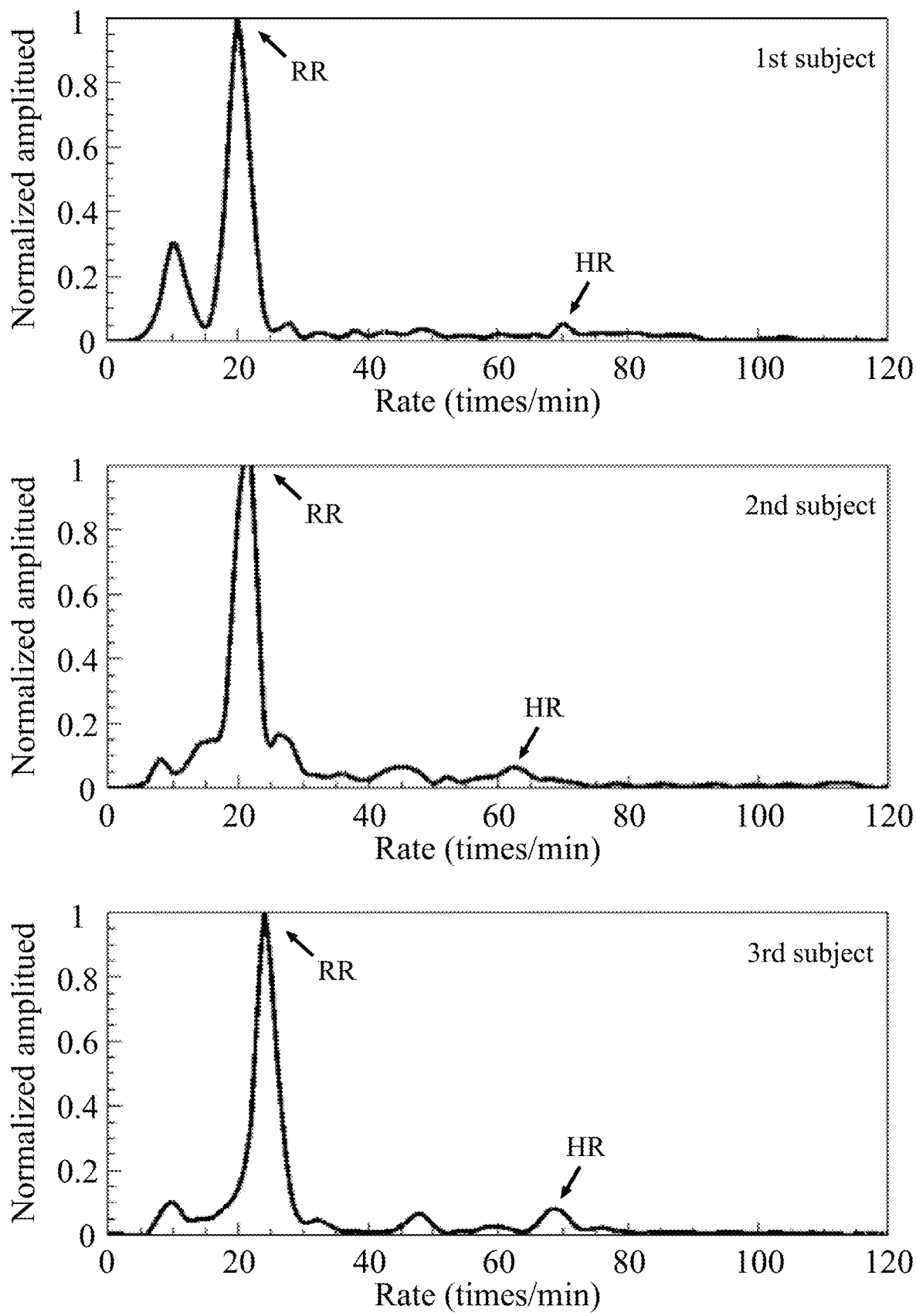
FIG. 12 shows the Doppler spectra obtained by the multiple-target vital sign detector in accordance with the second embodiment of the present invention.

FIGS. 11 and 12 are experimental results obtained by the multiple-target vital sign detector 100 of the second embodiment when the subjects 1-3 are at polar coordinate positions (135 cm, 70°), (210 cm, 110°) and (285 cm, 90°), respectively, relative to the multiple-target vital sign detector 100. FIG. 11 is a range-azimuth map constructed by the azimuth digital beamforming module 145 in the multiple-target vital sign processor 140, showing good agreement between the detected and actual positions of the subjects 1-3. The experimental results demonstrate that the multiple-target vital sign detector 100 of the second embodiment can measure the distance and azimuth of multiple subjects relative to the multiple-target vital sign detector 100. FIG. 12 displays the Doppler spectra extracted from the range azimuth map of FIG. 11 at the detected positions of the subjects 1-3. The RRs and HRs of the subjects 1-3 can be clearly identified in the Doppler spectra of FIG. 12, revealing that the multiple-target vital sign detector 100 of the second embodiment can simultaneously acquire positions and vital signs of multiple subjects.

While this invention has been particularly illustrated and described in detail with respect to the preferred embodiments thereof, it will be clearly understood by those skilled in the art that is not limited to the specific features shown and described and various modified and changed in form and details may be made without departing from the spirit and scope of this invention.

What is claimed is:

1. A multiple-target vital sign detector, comprising:
   a self-injection-locked oscillator (SILO) configured to generate an oscillation signal;
   a chirp up/down converter including a upconverting mixer, a transceiver antenna and a downconverting mixer, the upconverting mixer is electrically connected to the SILO and configured to convert the oscillation signal into a frequency-modulated continuous wave (FMCW) signal, the transceiver antenna is electrically connected to the upconverting mixer, configured to transmit the FMCW signal to an area as a transmitted signal and configured to receive a reflected signal from the area as a received FMCW signal, the downconverting mixer is electrically connected to the transceiver antenna and configured to convert the received FMCW signal into an injection signal, wherein the SILO is electrically connected to the downconverting mixer and configured to receive the injection signal to enter a self-injection-locked state;
   a frequency demodulator electrically connected to the SILO and configured to frequency-demodulate the oscillation signal to produce a frequency-demodulated signal; and
   a multiple-target vital sign processor electrically connected to the frequency demodulator and configured to sample and process the frequency-demodulated signal to construct a range-vital-Doppler map.

2. The multiple-target vital sign detector in accordance with claim 1, wherein the chirp up/down converter further includes a chirp signal generator that is configured to output a chirp signal, the upconverting mixer is electrically connected to the chirp signal generator, configured to convert the oscillation signal into the FMCW signal by mixing the oscillation signal with the chirp signal, the downconverting mixer is electrically connected to the chirp signal generator, configured to convert the received FMCW signal into the injection signal by mixing the received FMCW signal with the chirp signal.

3. The multiple-target vital sign detector in accordance with claim 2 further comprising a first power splitter, wherein the first power splitter is electrically connected to the SILO and configured to split the oscillation signal into two parts, one part of the oscillation signal is configured to be delivered to the upconverting mixer, and the other part of the oscillation signal is configured to be delivered to the frequency demodulator.

4. The multiple-target vital sign detector in accordance with claim 3, wherein the chirp up/down converter further includes a second power splitter that is electrically connected to the chirp signal generator and configured to split the chirp signal into two parts, one part of the chirp signal is configured to be delivered to the upconverting mixer, and the other part of the chirp signal is configured to be delivered to the downconverting mixer.

5. The multiple-target vital sign detector in accordance with claim 1, wherein the multiple-target vital sign processor includes a range-Doppler map (RDM) creating module that is configured to sample and process the frequency-demodulated signal to create an RDM.

6. The multiple-target vital sign detector in accordance with claim 5, wherein the multiple-target vital sign processor further includes a background subtraction module, an amplitude normalization module and a peak searching module, the background subtraction module is configured to eliminate a background of the RDM to create a background-subtracted RDM, the amplitude normalization module is configured to normalize the background-subtracted RDM in amplitude to create a normalized background-subtracted RDM, the peak searching module is configured to search for peaks above a certain threshold in the normalized background-subtracted RDM to construct a range-vital-Doppler map, wherein both range and vital sign frequency information are displayed simultaneously.

7. The multiple-target vital sign detector in accordance with claim 1, wherein the transceiver antenna includes a transmit antenna and a receive antenna, the transmit antenna is electrically connected to the upconverting mixer and configured to transmit the FMCW signal from the upconverting mixer to the area as the transmitted signal, the receive antenna is electrically connected to the downconverting mixer and configured to receive the reflected signal from the area as the received FMCW signal and deliver the received FMCW signal to the downconverting mixer.

8. The multiple-target vital sign detector in accordance with claim 7, wherein the receive antenna is a switched antenna array including a switch and a plurality of receive array antenna elements, the receive array antenna elements are configured to receive the reflected signal from the area as the received FMCW signal, the switch is electrically connected to the downconverting mixer and the receive array antenna elements and configured to switch one of the receive array antenna elements to couple to the downconverting mixer, the downconverting mixer is configured to convert the received FMCW signal into the injection signal, a phase shifter is electrically connected to the downconverting mixer and the SILO and configured to shift the phase of the injection signal by 0 or 90 degrees to produce a quadrature phase-shifted injection signal, the quadrature phase-shifted injection signal is configured to be injected into the SILO to make the SILO enter the self-injection-locked state.

9. The multiple-target vital sign detector in accordance with claim 8, wherein the SILO is configured to operate in the self-injection-locked state to generate a quadrature phase-shifted oscillation signal, a first power splitter is configured to split the quadrature phase-shifted oscillation signal into two parts, one part of the quadrature phase-shifted oscillation signal is configured to be delivered to the upconverting mixer for conversion into the FMCW signal, and the other part of the quadrature phase-shifted oscillation signal is configured to be delivered to the frequency demodulator, the frequency demodulator is configured to frequency-demodulate the quadrature phase-shifted oscillation signal to produce a quadrature frequency-demodulated signal.

10. The multiple-target vital sign detector in accordance with claim 9, wherein the multiple-target vital sign processor includes a range-Doppler map (RDM) creating module and an azimuth digital beamforming module, the RDM creating module is configured to sample and process the quadrature frequency-demodulated signal to create a plurality of RDMs corresponding to the receive array antenna elements, the azimuth digital beamforming module is coupled to the RDM creating module and configured to extract a range-azimuth map from the RDMs corresponding to the receive array antenna elements.

11. A detection method using a multiple-target vital sign detector, comprising:
generating an oscillation signal using a self-injection-locked oscillator (SILO);
performing conversion from the oscillation signal to an FMCW signal to detect an area and from a received FMCW signal reflected from the area to an injection signal using a chirp up/down converter, the chirp up/down converter includes a upconverting mixer, a transceiver antenna and a downconverting mixer, the upconverting mixer is electrically connected to the SILO and configured to convert the oscillation signal into the FMCW signal, the transceiver antenna is electrically connected to the upconverting mixer, configured to transmit the FMCW signal to the area as a transmitted signal and configured to receive a reflected signal from the area as the received FMCW signal, the downconverting mixer is electrically connected to the transceiver antenna and configured to convert the received FMCW signal into the injection signal;
injecting the injection signal into the SILO to achieve a self-injection-locked state of the SILO;
frequency-demodulating the oscillation signal to produce a frequency-demodulated signal using a frequency demodulator; and
sampling and processing the frequency-demodulated signal to construct a range-vital-Doppler map using a multiple-target vital sign processor.

12. The detection method in accordance with claim 11, wherein the multiple-target vital sign processor includes a range-Doppler map (RDM) creating module, a background subtraction module, an amplitude normalization module and a peak searching module, the RDM creating module is configured to sample and process the frequency-demodulated signal from the frequency demodulator to create an RDM, the background subtraction module is configured to eliminate a background of the RDM to create a background-subtracted RDM, the amplitude normalization module is configured to normalize the background-subtracted RDM in amplitude to create a normalized background-subtracted RDM, the peak searching module is configured to search for peaks above a certain threshold in the normalized background-subtracted RDM to construct the range-vital-Doppler map, wherein both range and vital sign frequency information are displayed simultaneously.

13. The detection method in accordance with claim 11, wherein the transceiver antenna includes a transmit antenna and a receive antenna, the transmit antenna is electrically connected to the upconverting mixer and configured to transmit the FMCW signal from the upconverting mixer to the area as the transmitted signal, the receive antenna is electrically connected to the downconverting mixer and configured to receive the reflected signal from the area as the received FMCW signal and deliver the received FMCW signal to the downconverting mixer.

14. The detection method in accordance with claim 13, wherein the receive antenna is a switched antenna array including a switch and a plurality of receive array antenna elements, the receive array antenna elements are configured to receive the reflected signal from the area as the received FMCW signal, the switch is electrically connected to the downconverting mixer and the receive array antenna elements and configured to switch one of the receive array antenna elements to couple to the downconverting mixer, the downconverting mixer is configured to convert the received FMCW signal into the injection signal, a phase shifter is electrically connected to the downconverting mixer and the SILO and configured to shift the phase of the injection signal by 0 or 90 degrees to produce a quadrature phase-shifted injection signal, the quadrature phase-shifted injection signal is configured to be injected into the SILO to make the SILO enter the self-injection-locked state.

15. The detection method in accordance with claim 14, wherein the SILO is configured to operate in the self-injection-locked state to generate a quadrature phase-shifted oscillation signal, the quadrature phase-shifted oscillation signal is configured to be split into two parts, one part of the quadrature phase-shifted oscillation signal is configured to be delivered to the upconverting mixer for conversion into the FMCW signal, and the other part of the quadrature phase-shifted oscillation signal is configured to be delivered to the frequency demodulator, the frequency demodulator is configured to frequency-demodulate the quadrature phase-shifted oscillation signal to produce a quadrature frequency-demodulated signal.

16. The detection method in accordance with claim 15, wherein the multiple-target vital sign processor includes a range-Doppler map (RDM) creating module and an azimuth digital beamforming module, the RDM creating module is configured to sample and process the quadrature frequency-demodulated signal from the frequency demodulator to create a plurality of RDMs corresponding to the receive array antenna elements, the azimuth digital beamforming module is coupled to the RDM creating module and configured to extract a range-azimuth map from the RDMs corresponding to the receive array antenna elements.

\* \* \* \* \*